United States Patent
Blatt et al.

(10) Patent No.: US 6,270,803 B1
(45) Date of Patent: Aug. 7, 2001

(54) CONTROLLED-RELEASE GARLIC FORMULATIONS

(75) Inventors: Yoav Blatt, Rehovot; David Cohen, Petach Tikva; Eugene Kimmelman, Rehovot; Oded Friedman, Holon; Avner Rotman, Rehovot, all of (IL)

(73) Assignee: Bio Dar Ltd., Yavne (IL)

( * ) Notice: Subject to any disclaimer, the term of this patent is extended or adjusted under 35 U.S.C. 154(b) by 0 days.

(21) Appl. No.: 09/392,754

(22) Filed: Oct. 7, 1998

(51) Int. Cl.[7] .................. A61K 9/14; A61K 9/42; A61K 9/22; A61K 9/16
(52) U.S. Cl. ............ 424/489; 424/476; 424/468; 424/494
(58) Field of Search .................... 424/489, 94.1, 424/451; 514/400

(56) References Cited

U.S. PATENT DOCUMENTS

| | | | |
|---|---|---|---|
| 4,849,218 | * | 7/1989 | Hess et al. ............ 424/94.1 |
| 5,405,616 | * | 4/1995 | Wunderlich et al. ...... 424/451 |
| 5,972,985 | * | 10/1999 | Thomas et al. .......... 514/400 |

FOREIGN PATENT DOCUMENTS

| | | |
|---|---|---|
| 35 41 304 | 5/1987 | (DE) . |
| 36 19 570 | 10/1987 | (DE) . |
| 38 01 025 | 7/1989 | (DE) . |
| 43 18 375 | 12/1994 | (DE) . |

OTHER PUBLICATIONS

HU 47 858, Kerbolt K., Apr. 28, 1989 (abstract).

* cited by examiner

*Primary Examiner*—Thurman K. Page
*Assistant Examiner*—Blessing Fubara
(74) *Attorney, Agent, or Firm*—Abelman, Frayne & Schwab

(57) ABSTRACT

There are provided orally-administrable formulations for the controlled release of granulated garlic, comprising particles of granulated garlic coated with a film comprising a mixture of at least one water soluble polymer and at least one water insoluble polymer, said at least one water soluble polymer and at least one water insoluble polymer being present in a ratio that produces a substantially zero order linear release pattern of at least one active ingredient. Preferably, the formulations are characterized in that the total in vitro dissolution time of said formulations required for release of 75% of the Allicin available from said formulations based upon the total amount of alliin initially present in said formulations is between about 4 and about 12 hours, as determined by U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C. A process for preparing the formulations of the invention is also disclosed.

31 Claims, 2 Drawing Sheets

CONTROLLED-RELEASE GARLIC FORMULATIONS

FIELD OF THE INVENTION

The present invention relates to formulations for the controlled or extended release of certain bioactive compounds, and to processes for the preparation of the same.

BACKGROUND OF THE INVENTION

Powdered and granulated garlic are good sources of allicin, γ-glutamyl peptides and certain other bioactive compounds. Allicin and γ-glutamyl peptides have broad and significant biological and therapeutic activities, including prevention of arteriosclerosis; lowering elevated levels of serum cholesterol and triglycerides; hypotensive effects; anticarcinogenic effects; antidiabetic effects; inhibition of platelet aggregation; and activation of fibrinolysis (Reuter & Sendl, "*Allium sativum* and *Allium ursinum*: Chemistry, Pharmacology, and Medicinal Applications", in: Economic and Medicinal Plant Research, Academic Press, New York, 1994, pp. 54–113; Koch & Hahn, "Knoblauch: Grundlagen der therapeutischen Anwendung von *Allium sativum L.*", Urban & Schwarzenberg, Munich 1988; Kochh & Lawson, "Garlic, The Science and Therapeutic Application of *Allium sativum L.* and Related Species", Williams & Wilkins 1996).

It has thus been established that Garlic powder and granules can serve as a important nutritional supplement, and that garlic, in the proper form, is a good source of those biologically active compounds which are believed to be responsible for the above-mentioned therapeutic effects. However, it has also been found that in garlic powder or granules which is stored for long periods, the active ingredients present in freshly ground garlic are often eliminated or otherwise rendered inactive.

SUMMARY OF THE INVENTION

The present invention seeks to provide an improved garlic preparation, which preparation offers a convenient oral dosage form of garlic for supplying optimum plasma concentrations of biologically active allicin and related compounds, and which facilitates user compliance with recommended procedures.

There is thus provided in accordance with a preferred embodiment of the invention an orally-administrable formulation for the controlled release of granulated garlic, comprising granulated garlic and at least one carrier, adjuvant or excipient therefor.

In one preferred embodiment of the invention, the orally-administrable formulation for the controlled release of granulated garlic comprises granulated garlic and at least one carrier, adjuvant or excipient therefor, and is characterized in that the total in vitro dissolution time of the formulation required for release of 75% of the Allicin available from the formulation, based upon the total amount of alliin initially present in the formulation, is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C.

In one preferred embodiment of the invention, the formulation is characterized in that it contains from 1 to 95 wt. % granulated garlic.

In another preferred embodiment of the invention, the formulation is in a form selected from the group consisting of a matrix tablet, a multicomponent formulation, a microcapsule of generally spherical shape, a microcapsule of generally non-spherical shape, a capsule containing microcapsules, and a tablet containing microcapsules.

In another preferred embodiment of the invention, the formulation comprises granulated garlic mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes, sugars and sugar alcohols.

In one preferred embodiment of the invention, the formulation is in the form of a tablet comprising granulated garlic embedded in a mixture of polyvinyl chloride and polyvinyl acetate, and magnesium stearate as a lubricant.

In another preferred embodiment of the invention, the formulation is in the form of a tablet comprising granulated garlic embedded in a mixture of polyvinyl chloride and ethyl cellulose, magnesium stearate as lubricant, and a material selected from hydroxypropyl methyl cellulose, sodium carboxymethyl cellulose and paraffin.

In a preferred embodiment of the invention, the formulation is in the form of a hard gelatin two-piece capsule filled with microcapsules containing granulated garlic.

In another preferred embodiment of the invention, the formulation is in the form of a tablet comprising microcapsules.

The invention also comprises a process for the preparation of an orally-administrable formulation for the controlled release of granulated garlic, said preparation comprising granulated garlic and at least one carrier, adjuvant or excipient therefor, said process comprising the steps of:

providing granulated garlic; and incorporating said granulated garlic into said at least one carrier, adjuvant or excipient therefor;

wherein said at least one carrier, adjuvant or excipient therefor is characterized in that the total in vitro dissolution time of said formulation required for release of 75% of the Allicin from said formulation based upon the total amount of alliin initially present in said formulation is between about 4 and about 18 hours, as determined by to the U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C.

In one preferred embodiment of the invention, the process is characterized in that the granulated garlic is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes, sugars and sugar alcohols, and (ii) then compressed into tablets.

In another preferred embodiment of the invention, the process is characterized in that the granulated garlic is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes and sugars, (ii) then processed into a form selected from the group of microcapsules and pellets, and (iii) the microcapsules or pellets are filled into hard gelatin capsules.

In a preferred embodiment of the invention, the process is characterized in that the granulated garlic is (i) mixed or coated with an adjuvant or mixture of adjuvants selected from the group consisting of synthetic polyvinyl-type polymers, synthetic polyethylene-type polymers, cellulose-type polymers, synthetic polyacrylate-type polymers, fats, waxes and sugars, (ii) then processed into a form selected from the group of microcapsules and pellets, and (iii) said microcapsules or pellets are compressed into tablets.

There is also provided in accordance with a preferred embodiment of the invention an orally-administrable formulation for the controlled release of granulated garlic, comprising particles of granulated garlic coated with a film comprising a mixture of at least one water soluble polymer and at least one water insoluble polymer, the at least one water soluble polymer and the at least one water insoluble polymer being present in a ratio that produces a substantially zero order linear release pattern of at least one active ingredient. In one preferred embodiment of the invention, the particles comprise particles which are non-spherically shaped. In another preferred embodiment of the invention, the particles comprise particles which are spherically shaped.

In a preferred embodiment of the invention, the at least one active ingredient is allicin. In another preferred embodiment of the invention, the at least one active ingredient is alliin.

There is also provided in accordance with a preferred embodiment of the invention an orally-administrable formulation for the controlled release of granulated garlic, comprising particles of granulated garlic coated with an enteric coating comprising a polymer film comprising a polymer which is insoluble at a pH below about 5.5. In a preferred embodiment of the invention, the particles comprise particles which are non-spherically shaped. In another preferred embodiment of the invention, the particles comprise particles which are spherically shaped.

In a preferred embodiment of the invention, the polymer is soluble at a pH of about 5.5 or higher. In another preferred embodiment of the invention, the polymer is insoluble at a pH below about 5.0.

In one preferred embodiment of the invention, the polymer is hydroxypropylmethyl cellulose phthalate. In another preferred embodiment of the invention, the polymer is cellulose acetate phthalate.

In a preferred embodiment of the invention, the water insoluble polymer is ethyl cellulose.

In another preferred embodiment of the invention, the water soluble polymer is hydroxypropylmethyl cellulose (HPMC).

In a preferred embodiment of the invention, the water insoluble polymer is ethyl cellulose and the water soluble polymer is hydroxypropymethyl cellulose (HPMC), and the HPMC/ethyl cellulose ratio is substantially from about 0.005 to about 0.40.

In a preferred embodiment of the invention, the content of granulated garlic is between about 1 to 95 wt. %.

In accordance with another preferred embodiment of the invention, there is provided a process for producing an orally-administrable formulation for the controlled release of granulated garlic, comprising coating particles of granulated garlic with an inner, mixed polymer film comprising ethyl cellulose and hydroxypropylmethyl cellulose (HPMC), wherein the HPMC/ethyl cellulose ratio is substantially from about 0 to about 0.40 by weight, and then coating said particles coated with said inner polymer film with an outer polymer film comprising hydroxypropylm-ethyl cellulose phthalate, wherein the weight ratio of the outer and inner polymer layers is between about 0.5 to 1.5.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS OF THE INVENTION

Figure 1:
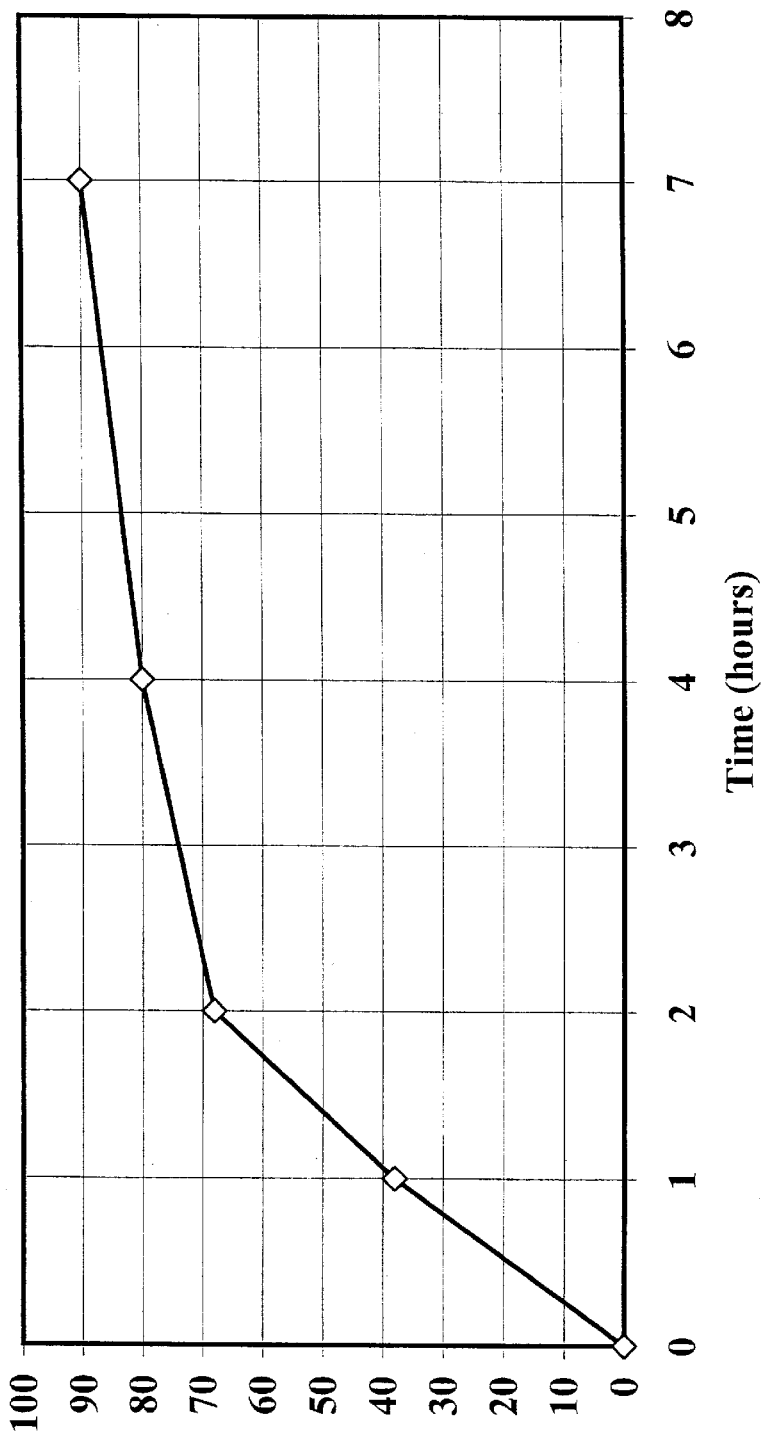
FIG. 1 shows the allicin release characteristics of granulated garlic particles microencapsulated in accordance with a preferred embodiment of the present invention, under simulated intestinal conditions.

In the context of the foregoing and subsequent description, including the claims, the term "granulated garlic" will be understood to refer to both powdered and granulated garlic, i.e. garlic which has been ground to a particle size within the range of about 100 and about 2000 $\mu$m diameter, preferably in the range of about 300 and about 1000 $\mu$m diameter.

The oral controlled release dosage formulations of granulated garlic, in accordance with the invention, include matrix formulations, such as matrix tablets, and multiparticulate formulations such as microcapsules.

Garlic contains both the enzyme alliinase and, separated from the alliinase, alliin, which is the enzyme's substrate. Alliinase converts two molecules of alliin into one molecule of allicin. As will be shown below, the in vitro dissolution time for release of 75% of the allicin which can be formed, based on the amount of alliin initially present in the oral controlled release dosage forms of granulated garlic in accordance with the present invention (hereinafter referred to as "75% alliin-equivalent allicin"), is between 4–18 hours, as determined according to the U.S.P. XXIII paddle method (with some modifications, as will be described hereinbelow).

In one preferred formulation of the invention, non-spherically shaped garlic particles are coated with double film layers: the first (inner) layer comprises a water insoluble polymer such as ethylcellulose and a water soluble polymer such as hydroxypropylmethyl cellulose (HPMC) in an HPMC/ethylcellulose weight ratio substantially within the range of 0 to 0.4. The second (outer) layer comprises polymers the solubilities of which are pH-dependent, such as hydroxypropylmethyl cellulose phthalate, which are soluble only at a pH higher than 5.5, and are therefore insoluble at a pH comparable to that found in the human stomach.

The present invention relates to oral controlled and stable release dosage form of granulated garlic, especially in either matrix formulations such as matrix tablets or ion multiparticulate formulations like microcapsules put into two piece capsules. This is done in order to obtain a drug delivery system of garlic-derived molecules which will ensure a steady supply of the active component for a sustained period. By either embedding the granulated garlic into a matrix formulation or incorporating it into a microcapsule formulation, or both, in order to control or extend the release of the components of the garlic into the surroundings, the following advantages may be obtained in comparison with conventional release formulations:

A slower in vivo absorption of garlic-derived active molecules, and hence optimal plasma peak values, which thus reduces the occurrence of undesired effects often associated with ingestion of garlic, such as an unpleasant garlic odor emanating from the person who ingested the garlic.

Prolonged and steady plasma concentrations of garlic-derived active molecules over 12 hours, which can help avoid underdosing between dosage intervals.

A significant increase in the relative extent of bioavailability (amount of active ingredient per gram of garlic ingested) of garlic-derived active molecules, i.e. the therapeutically relevant component, in comparison to standard release formulations.

Higher tolerability of the active ingredients, i.e. fewer side effects.

Reduction in the number of daily doses required, which together with the higher tolerability can significantly increase user compliance.

Stabilization of the highly sensitive garlic-derived active ingredients and thus extending the shelf life of the product.

Provision of an enteric-coated formulation wherein the enzyme alliinase reacts with its substrate alliin only in the intestine, where the pH is at least 6 and thus the alliinase is not destroyed.

Coating and Matrix Materials for Obtaining Enteric Coated and Controlled Release Coating and matrix materials which may be used in accordance with the invention are those known in the art for use in controlled-release formulations, such as:

(a) synthetic polymers of the polyvinyl type, e.g. polyvinylchloride, polyvinylacetate and copolymers thereof, polyvinylalcohol, and polyvinylpyrrolidone;

(b) synthetic polymers of the polyethylene type, e.g. polyethylene and polystyrene;

(c) polymers of the acrylic acid or acrylic acid ester type, e.g. methylmethacrylate or copolymers of acrylic monomers;

(d) biopolymers or modified biopolymers, such as cellulose or cellulose derivatives, e.g. ethylcellulose, cellulose acetate phthalate, cellulose acetate, hydroxypropyl cellulose, hydroxypropylmethyl cellulose, methylcellulose, microcrystalline cellulose, Na-carboxymethyl cellulose, as well as, for example, shellac and gelatin;

(e) fats, oils, higher fatty acids and higher alcohols (i.e. acids and alcohols containing alkyl chains of at least 10 carbon atoms), e.g. aluminum monostearate, cetylalcohol, hydrogenated beef tallow, hydrogenated castor oil, 12-hydroxystearyl alcohol, glyceryl mono- or dipalmiate, glyceryl mono-, di- or tristearate, myristyl alcohol, stearic acid, stearyl alcohol, and polyethyleneglycols;

(f) waxes, e.g. bees' wax, carnauba wax, Japan wax, paraffin, spermaceti, and synthetic waxes; and (g) sugars and sugar alcohols, e.g. mannitol, sorbitol, sucrose, xylitol, glucose, and maltose.

Depending on the technique used, the polymers mentioned above can be used as coating agents, matrix adjuvants or pharmaceutical binders. Whether the polymer will function as a matrix adjuvant or a pharmaceutical binder will be dependent on the amount of polymer in the formulation.

Combinations of the above mentioned polymers, fats and waxes can also be used for encapsulation purposes as well as for matrix formation, viz. different polymers can be mixed, a polymer can be mixed with a fat or wax, and so forth.

The encapsulation of the drug can be achieved in the form of microcapsules, but the encapsulation is not restricted to the micro size, i.e. the range of 50 $\mu$m to 2000 $\mu$m.

The multiparticulate dosage forms, i.e., microcapsules or coated pellets as well as the matrix tablets useful for the present invention can be prepared by any of several known production processes, including conventional granulation and tableting of matrix tablets, pan coating, prilling, extrusion and spheronization, fluid bed processes, spray drying, spray chilling, coacervation and other processes.

Microcapsules or coated pellets

Microcapsules or coated pellets are defined as a solid or liquid core enclosed in a coating. The coating may also be referred to as the wall or shell. Various types of microcapsule structures can be obtained depending on the manufacturing process, e.g. mononuclear spherical, multinuclear spherical, multinuclear irregular, encapsulated mononuclear capsules, dual-walled microcapsules, etc. Where no distinct coating and core region can be observed, the analogous terms are microparticles, microspheres, micromatrices, and microbeads. The microcapsules or pellets of the present invention usually have a particle size between about 1 and about 2000 microns.

The microcapsules or coated pellets of granulated garlic can be filled into empty hard gelatin capsules to an extent corresponding to the desired dose, or they can be gently compressed into a tablet by using suitable tablet excipients.

Coated garlic particles may also be mixed with a pharmaceutical binder to form micropellets, which are then compressed into tablets.

The orally administrable formulations of the invention may comprise micropellets, which are then coated with a pharmaceutically acceptable coating adjuvant prior to being compressed into tablets. The micropellets can also be filled into capsules.

The formulations of the invention may also comprise microspheres which are then coated with a pharmaceutically acceptable coating adjuvant prior to being filled into capsules.

Matrix formulations

Matrix formulations are defined as a drug or other active ingredient embedded in insoluble excipients in order to achieve extended release by a continuous leaching of the drug from the inert matrix core. The release mechanisms often follows the square root law of Higuchi. This term also applies to a matrix built of hydrophilic substances which in contact with water form a gel of high viscosity.

One type of matrix formulation is a matrix tablet, which is a matrix formulation in tablet form. Such tablets may be coated with an enteric coating, which inhibits or prevents dissolution of the tablets at low pH (below about pH 5, preferably below about pH 5.5), such as is found in the stomach, and enables dissolution of the tablets at higher pH's (e.g. around pH 6.8, such as is found in the intestine).

EXAMPLES

In one preferred embodiment of the present invention, granulated garlic is embedded in hydroxypropyl methyl cellulose and then compressed into a tablet formulation using magnesium stearate as lubricant (round tablet, 6–8 mm in diameter).

In other preferred embodiments of the invention, granulated garlic is embedded in a mixture of polyvinyl chloride and ethyl cellulose, with the addition of hydroxypropyl methyl cellulose, sodium carboxymethyl cellulose or paraffin. The material is then compressed into tablets, using magnesium stearate as lubricant.

In other preferred embodiments of the invention, granulated garlic is suspended in a wax melt, e.g. carnauba wax, bees' wax or the like, and then spray chilled into microspheres. The spherical particles can then be coated with a fat or fatty acid, polyethylene glycol or a low melting wax by suspending the microspheres in the low melting excipient and then once again spray chill the slurry into microcapsules.

The invention will be better understood through the following illustrative and non-limitative Examples.

Example 1

Controlled release granulated garlic was prepared by coating dried garlic granules, which had been dried at room temperature or below, of average diameter in the range of about 300 to 1000 μm, with a semipermeable membrane as follows: First, 2.94 kg of dried garlic granules were fluidized in a modified fluid bed coater (GPCG3, Glatt). The inlet temperature was adjusted to achieve a product temperature of 27° C. The granules were then sprayed with a solution made according to the list below:

| | |
|---|---|
| Acetone: | 2760 g |
| Isopropanol | 324 g |
| Ethyl cellulose | 559.28 g |
| Castor oil: | 57.5 g |

The speed of spraying was adjusted in order to obtain a good and homogeneous film on the garlic granules. The preparation was tested for its slow release properties by dissolution using a U.S.P. apparatus II (paddles, as described in U.S.P. XXIII) in 900 ml simulated intestinal fluid (without the digestive enzymes normally found in intestinal fluid), containing 0.1% w/w sodium dodecyl sulfate (SDS), at pH 6.8, a temperature of 37° C. and a paddle speed of 150 rpm. Samples were withdrawn at several time intervals and analyzed by HPLC for Allicin content.

As illustrated in FIG. 1, this preparation afforded slow release of Allicin into medium; within the first hour, between 30 to 50% of the total amount of allicin available, based on the amount of alliin initially present, was released; in the first 2 hours, between about 50 and 70% of the total amount of allicin available based on the amount of alliin initially present; in the first 4 hours, between about 70 and 80% of the total amount of allicin available based on the amount of alliin initially present; and in the first 6 hours, more than 75% of the total amount of allicin available based on the amount of alliin initially present.

Example 2

Garlic granules (particle size in the range of 300–1000 μm) were coated as in Example 1. Some of these coated granules (750 g) were then further coated with a second layer of polymer solution made according to the list below:

Acetone: 236 g

Isopropanol: 236 g

HP-55 (Hydroxypropylmethyl cellulose phthalate): 69.5 g

Castor oil: 7.33 g

The speed of spraying was adjusted in order to obtain a good and homogeneous film on the granules. The preparation was tested for its slow release and enteric coated properties by dissolution using a U.S.P. apparatus II (paddles, as described in U.S.P. XXIII) in 750 ml simulated gastric fluid (0.1 M HCl, pH=1.5) for 1 hour, and then pH was adjusted to 6.8 by the addition of 250 ml of a solution of trisodium phosphate containing 1 g of SDS. The temperature was kept at 37° C. and the paddle speed at 150 rpm. Samples were withdrawn at several time intervals and analyzed by HPLC for Allicin content.

Figure 2:
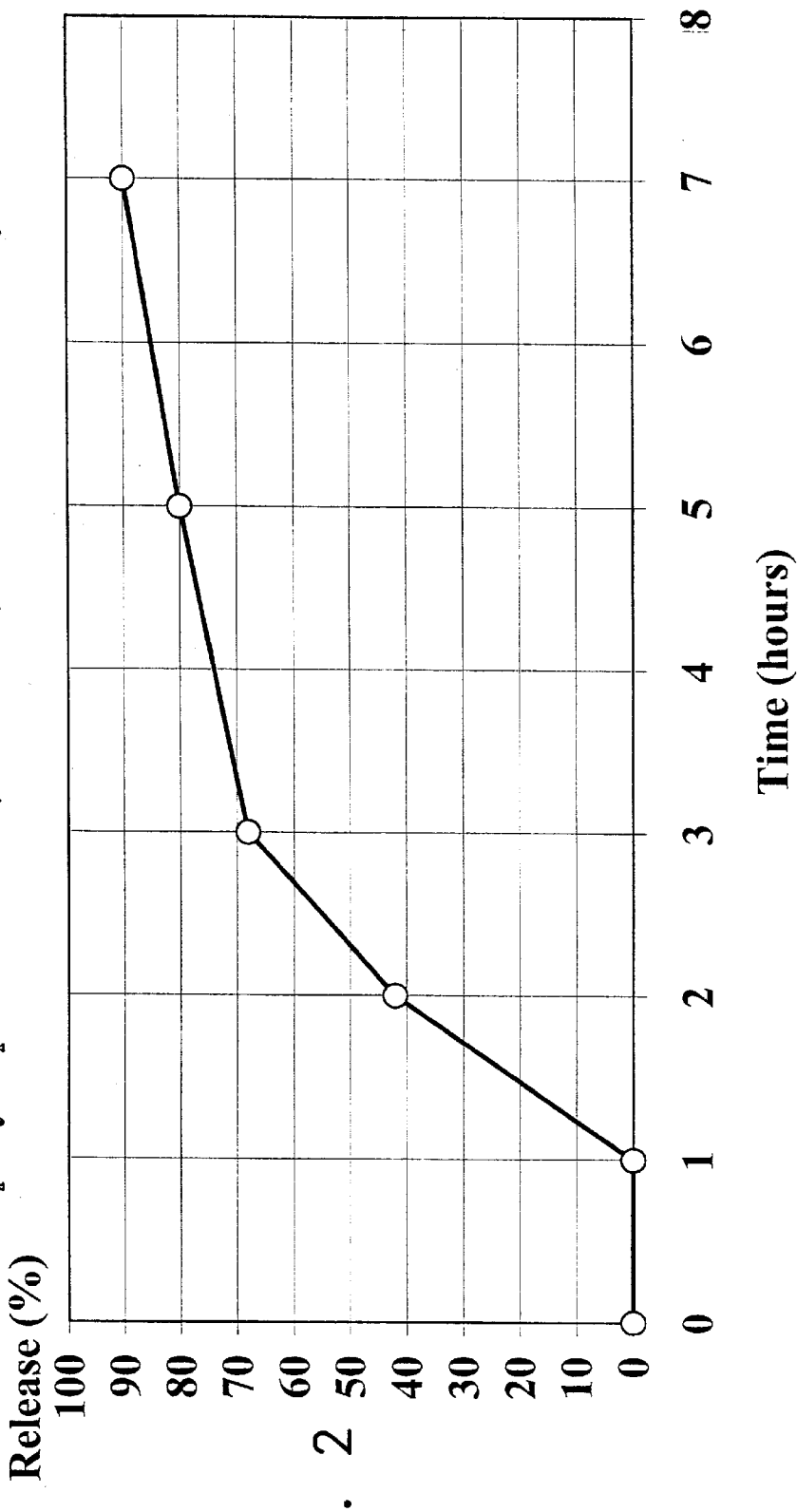
FIG. 2 shows the allicin release characteristics of granulated garlic particles microencapsulated in accordance with another preferred embodiment of the present invention, under simulated intestinal conditions.

As illustrated in FIG. 2, during the first hour, while the pH was comparable to that of gastric medium, the preparation did not release any Allicin. Following the increase of pH to 6.8 (comparable to the pH of intestinal fluid), between about 40% and about 50% of the total amount of allicin that could be produced, based on the amount of alliin initially present in the preparation, was released in the first hour after pH increase, between about 50% and about 70% of the total amount of allicin that could be produced was released in the first 2 hours after the pH increase, and approximately 90% of the total amount of allicin that could be produced was released within 6 hours after the pH increase.

Example 3

The release of allicin from formulations prepared and dissolved in accordance with Example 2 (release in simulated intestinal media, pH=6.8, following a 1 hour incubation in simulated gastric fluid) was compared with the release of allicin from five commercially available granulated garlic formulations dissolved under the same conditions. The amounts of garlic contained in each formulation, the amount of allicin equivalents indicated by the manufacturer as being present, the amount of allicin actually found, and the amount of allicin released per gram of garlic are tabulated in Table 1 below.

TABLE 1

| | | | Allicin | |
|---|---|---|---|---|
| Source | Recommended Daily Dose (garlic equivalent, mg) | Declared (mg) | Found (mg) per recommended daily dose | mg allicin found per 1 g garlic |
| Brand A | 1500 | NA* | 0.000 | 0.000 |
| Brand B | 600 | NA | 0.000 | 0.000 |
| Brand C | 500 | 0.75 | 0.075 | 0.150 |
| Brand D | 3600 | 3.60 | 1.050 | 0.292 |
| Brand E | 3600 | NA | 1.590 | 0.442 |
| Present Invention | 300 | NA | 1.000 | 3.333 |

*NA = information not available

It will be readily appreciated from the results shown in Table 1 that use of the invention enables significantly greater amounts of allicin per dose of garlic to be released than use of formulations hitherto known in the art. The greater degree of release of biologically active molecules per amount of garlic, coupled with the sustained release characteristics of the invention, indicate that the present invention can be used to optimize bioavailability of the garlic-derived biologically compounds, and to increase compliance of the user with the dosage regimen by minimizing the number of daily dosages required and helping avoid underdosing between dosage intervals. The invention enables slower in vivo absorption of garlic-derived active molecules, and hence optimal plasma peak values, which thus reduces the occurrence of undesired effects often associated with ingestion of garlic, such as an unpleasant garlic odor emanating from the person who ingested the garlic.

Example 4

Dried granulated garlic was left both untreated and microencapsulated as described in Example 2. Samples were then left for 6 months at both room temperature and humidity, and under accelerated conditions of 40° C. and 75% relative humidity. At the end of six month, samples were analyzed for the percentage of alliin lost over the period under the specified conditions. The results are shown in Table 2.

TABLE 2

| Sample | % Alliin lost after six months: | |
|---|---|---|
| | At Room Temperature & Humidity | At 40° C. and 75% Relative Humidity |
| Untreated | 25 | 65 |
| Microencapsulated | 10 | 18 |

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the invention is defined only by the claims which follow.

What is claimed is:

1. An orally-administrable formulation for the controlled release of granulated garlic, consisting essentially of microencapsulated granulated garlic particles which have been microencapsulated by direct coating with an enteric coating and at least one pharmaceutically acceptable diluent, adjuvant or excipient therefor.

2. An orally-administrable formulation for the controlled release of granulated garlic according to claim 1, comprising microencapsulated granulated garlic particles which have been microencapsulated by direct coating with an enteric coating and at least one pharmaceutically acceptable diluent, adjuvant or excipient therefor, characterized in that the total in vitro dissolution time of said formulation required for release of 75% of the Allicin available from said formulated based upon the total amount of alliin initially present in said formulation is between about 4 and about 18 hours, as determined by the U.S.P. XXIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C.

3. A formulation according to claim 1 characterized in that it contains from 1 to 95 wt. % granulated garlic.

4. A formulation according to claim 1, wherein said formulation is in a form selected from the group consisting of: a matrix tablet, a multicomponent formulation, a microcapsule of generally spherical shape, a microcapsule of generally non-spherical shape, a capsule containing microcapsules, and a tablet containing microcapsules.

5. A formulation according to claim 1 comprising granulated garlic mixed or coated with an adjuvant or mixture of adjuvants selected from the group consisting of synthetic polyvinyl polymers, synthetic polyethylene polymers, cellulose polymers, synthetic polyacrylate polymers, fats, waxes, sugars and sugar alcohols.

6. A formulation according to claim 1 in the form of a tablet comprising:

granulated garlic embedded in a mixture of polyvinyl chloride and polyvinyl acetate;

and magnesium stearate as a lubricant.

7. A formulation according to claim 1 in the form of a tablet comprising:

granulated garlic embedded in a mixture of polyvinyl chloride and ethyl cellulose;

magnesium stearate as lubricant; and a material selected from hydroxypropyl methyl cellulose, sodium carboxymethyl cellulose and paraffin.

8. A formulation according to claim 1 in the form of a hard gelatin two-piece capsule filled with microcapsules containing granulated garlic.

9. A formulation according to claim 1 in the form of a tablet comprising microcapsules.

10. A process for the preparation of an orally-administrable formulation for the controlled release of granulated garlic, said preparation comprising microencapsulated granulated garlic particles which have been microencapsulated by being directly coated with an enteric coating and at least one diluent, adjuvant or excipient therefor, said process comprising the steps of:

providing granulated garlic particles; and microencapsulating said granulated garlic particles by coating said granulated garlic particles with at least one diluent, adjuvant or excipient therefor, wherein said at least one diluent, adjuvant or excipient therefor also functions as an enteric coating.

11. The process according to claim 10 characterized in that said granulated garlic is (i) coated with an adjuvant or mixture of adjuvants selected from the group consisting of synthetic polyvinyl polymers, synthetic polyethylene polymers, cellulose polymers, synthetic polyacrylate polymers, fats, waxes, sugars and sugar alcohols, and (ii) then compressed into tablets.

12. A process for the preparation of an orally-administrable formulation according to claim 10 and wherein:

said formulation is characterized in that the total in vitro dissolution time of said formulation required for release of 75% of the Allicin from said formulation based upon the total amount of alliin initially present in said formulation is between about 4 and about 18 hours, as determined by the U.S.P. XXIIII paddle method at a paddle speed of 150 rpm, using simulated intestinal fluid without the digestive enzymes normally found in intestinal fluid, containing 0.1% w/w sodium dodecyl sulfate (SDS), at pH 6.8, and a temperature of 37° C.

13. The process according to claim 11 characterized in that said granulated garlic is (i) coated with an adjuvant or mixture of adjuvants selected from the group consisting of synthetic polyvinyl polymers, synthetic polyethylene polymers, cellulose polymers, synthetic polyacrylate polymers, fats, waxes and sugars, (ii) then processed into a form selected from the group of microcapsules and pellets, and (iii) said microcapsules or pellets are filled into hard gelatin capsules.

14. The process according to claim 11 characterized in that said granulated garlic is (i) coated with an adjuvant or mixture of adjuvants selected from the group consisting of synthetic polyvinyl polymers, synthetic polyethylene polymers, cellulose polymers, synthetic polyacrylate polymers, fats, waxes and sugars, (ii) then processed into a form selected from the group of microcapsules and pellets, and (iii) said microcapsules or pellets are compressed into tablets.

15. An orally-administrable formulation for the controlled release of granulated garlic, consisting essentially of particles of granulated garlic directly coated with a film comprising a mixture of at least one water soluble polymer and at least one water insoluble polymer, said at least one water soluble polymer and at least one water insoluble polymer being present in a ratio that produces a substantially zero order linear release pattern of at least one active ingredient.

16. An orally-administrable formulation according to claim 15, wherein said particles comprise particles which are non-spherically shaped.

17. An orally-administrable formulation according to claim 15, wherein said particles comprise particles which are spherically shaped.

18. An orally-administrable formulation according to claim 15, wherein said at least one active ingredient is allicin.

19. An orally-administrable formulation according to claim 15, wherein said at least one active ingredient is alliin.

20. A formulation according to claim 15 wherein said water insoluble polymer is ethyl cellulose.

21. A formulation according to claim 15 wherein said water soluble polymer is hydroxypropylmethyl cellulose (HPMC).

22. A formulation according to claim 15 wherein said water insoluble polymer is ethyl cellulose and said water soluble polymer is hydroxypropymethyl cellulose (HPMC), and wherein the HPMC/ethyl cellulose ratio is substantially from about 0.05 to about 0.40.

23. A formulation according to claim 15 wherein the content of granulated garlic is between about 1 to 95 wt. %.

24. An orally-administrable formulation for the controlled release of granulated garlic, consisting essentially of particles of granulated garlic directly coated with an enteric coating comprising a polymer film comprising a polymer which is insoluble at a pH below about 5.5.

25. An orally-administrable formulation according to claim 24, wherein said particles comprise particles which are non-spherically shaped.

26. An orally-administrable formulation according to claim 24, wherein said particles comprise particles which are spherically shaped.

27. A formulation according to claim 24, wherein said polymer is soluble at a pH of about 5.5 or higher.

28. A formulation according to claim 24, wherein said polymer is insoluble at a pH below about 5.0.

29. A formulation according to claim 24, wherein said polymer is hydroxypropylmethyl cellulose phthalate.

30. A formulation according to claim 24, wherein said polymer is cellulose acetate phthalate.

31. A process for producing an orally-administrable formulation for the controlled release of granulated garlic, comprising microencapsulating granulated garlic particles by directly coating said granulated garlic particles with an inner, mixed polymer film comprising ethyl cellulose and hydroxypropylmethyl cellulose (HPMC), wherein the HPMC/ethyl cellulose ratio is substantially from about 0 to about 0.40 by weight, and then coating said particles coated with said inner polymer film with an outer polymer film comprising hydroxypropylmethyl cellulose phthalate, wherein the weight ratio of the outer and inner polymer layers is between about 0.5 to 1.5.

* * * * *